(12) United States Patent
Kotzev

(10) Patent No.: US 7,125,942 B2
(45) Date of Patent: Oct. 24, 2006

(54) ACRYLIC ESTERS OF 2-CYANO-2, 4 PENTENEDIOIC ACID

(76) Inventor: Dimiter Lubomirov Kotzev, 21 Carron Close, Corby, Northants NN17 2LB (GB)

( * ) Notice: Subject to any disclaimer, the term of this patent is extended or adjusted under 35 U.S.C. 154(b) by 265 days.

(21) Appl. No.: 10/802,074

(22) Filed: Mar. 15, 2004

(65) Prior Publication Data

US 2004/0249099 A1    Dec. 9, 2004

Related U.S. Application Data

(63) Continuation of application No. 09/131,275, filed on Aug. 10, 1998, now abandoned.

(60) Provisional application No. 60/055,791, filed on Aug. 15, 1997.

(51) Int. Cl.
*C08F 20/52*    (2006.01)
(52) U.S. Cl. ...................................... 526/298; 524/555
(58) Field of Classification Search ................ 524/555; 526/298
See application file for complete search history.

(56) References Cited

U.S. PATENT DOCUMENTS

| 3,316,227 A | 4/1967 | Gerber |
| 3,554,990 A | 1/1971 | Quinn et al. |
| 4,425,471 A | 1/1984 | Millet |

OTHER PUBLICATIONS

Trofimov et al., "Synthesis of 2-Cyanopenta-2, 4-dienoic acid esters," Journal Vases. Him. O-Va. (1974) 19(4), AN 1974:551489.

*Primary Examiner*—Bernard Lipman

(57) ABSTRACT

The invention relates to reactive monomers containing 2-cyanopenta-2,4-dienoate and methacrylic or acrylic double bonds in their molecules. The reactive monomers are easily polymerizable in a variety of ways. The polymerized reactive monomers can form strong adhesive bonds between a variety of substrates. The adhesive bonds are water and humidity resistant, heat resistant, impact and peel resistant and can sustain large loads and stresses. The polymerized reactive monomers are applicable as structural and industrial adhesives, medical and surgical adhesives and optical fiber coatings, and can be used in the manufacture of positive or negative photo or electron beam resists.

6 Claims, 5 Drawing Sheets

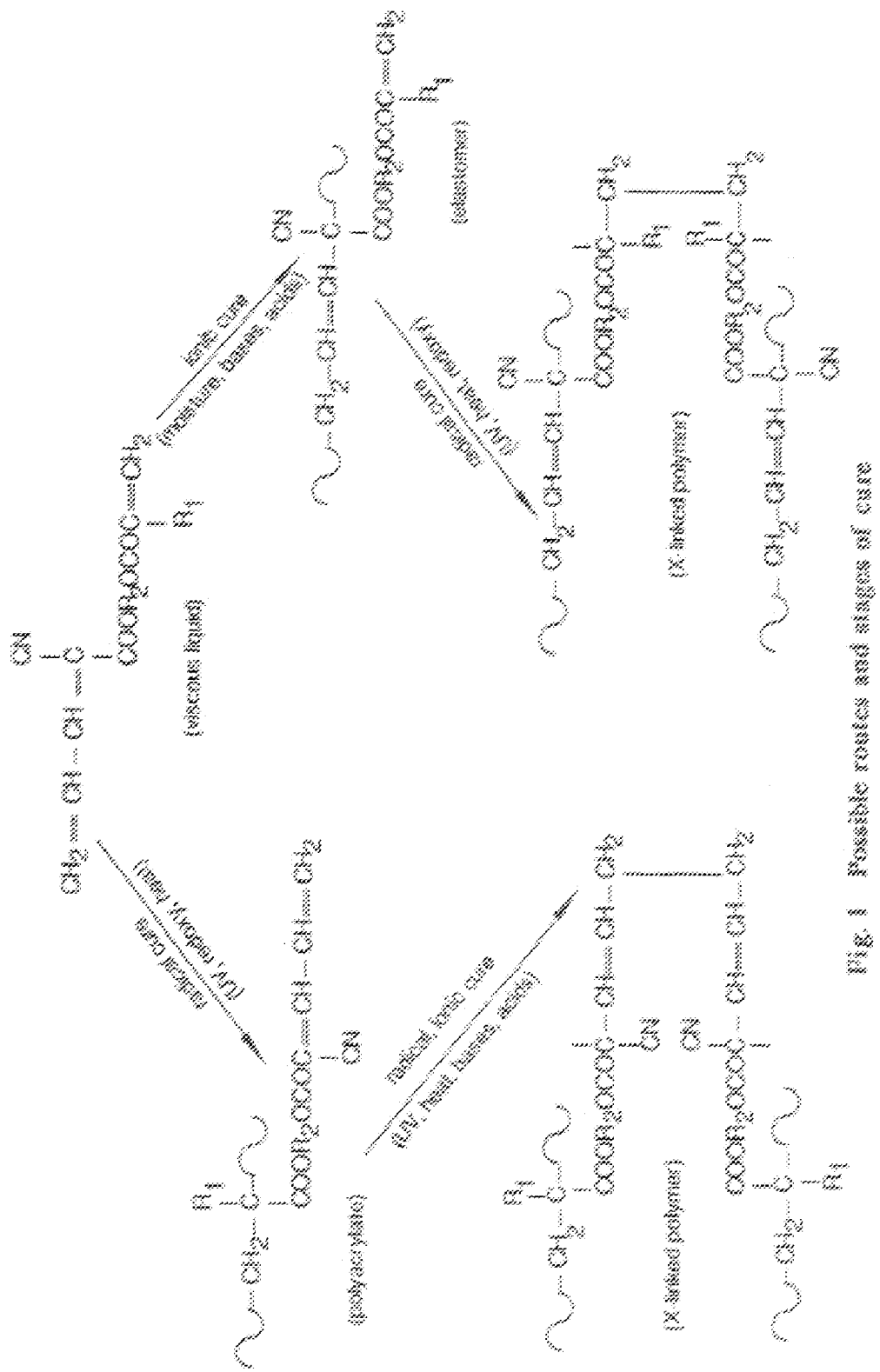
Fig. 1 Possible routes and stages of cure

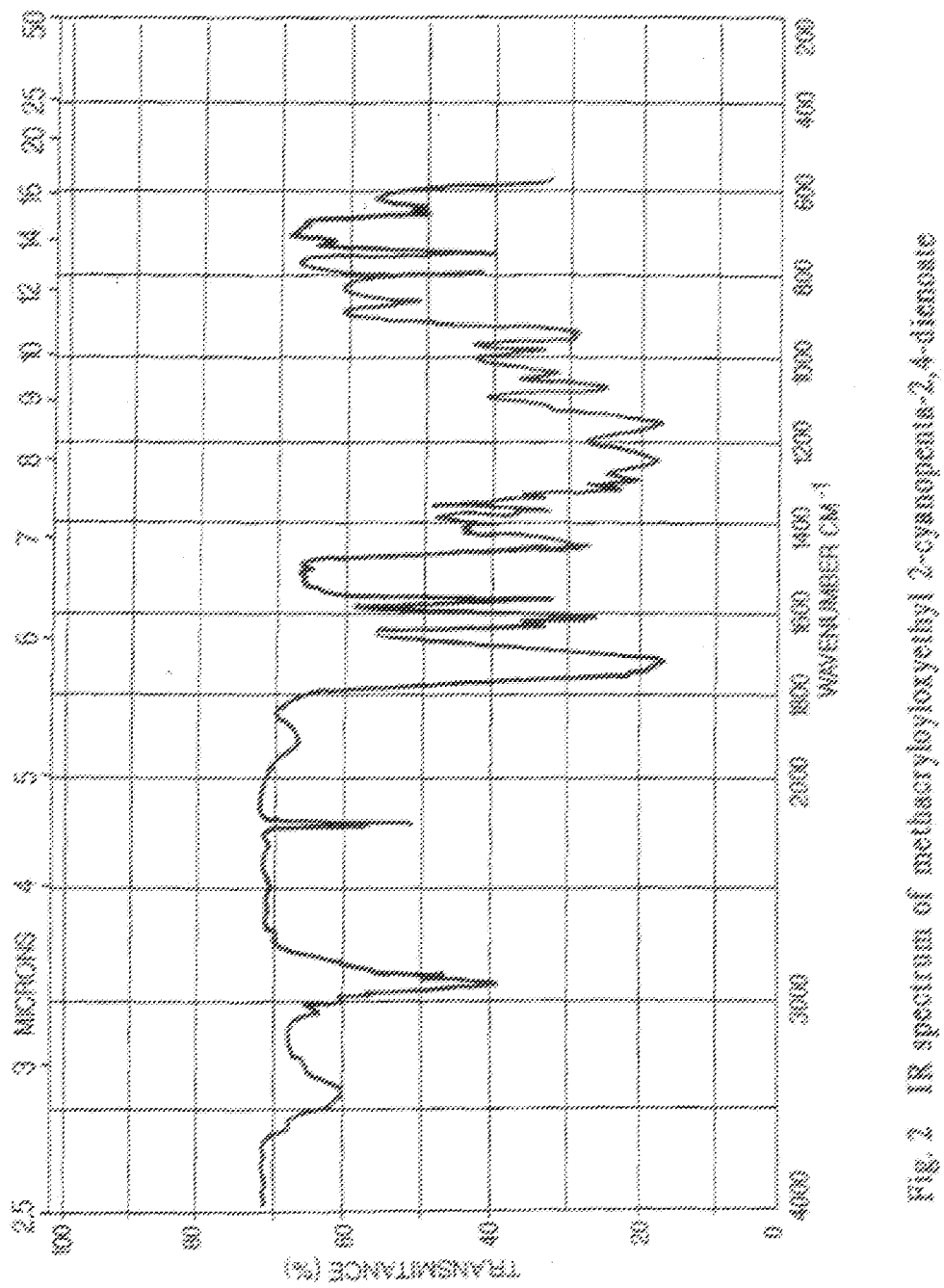
Fig. 2 IR spectrum of methacryloyloxyethyl 2-cyanopenta-2,4-dienoate

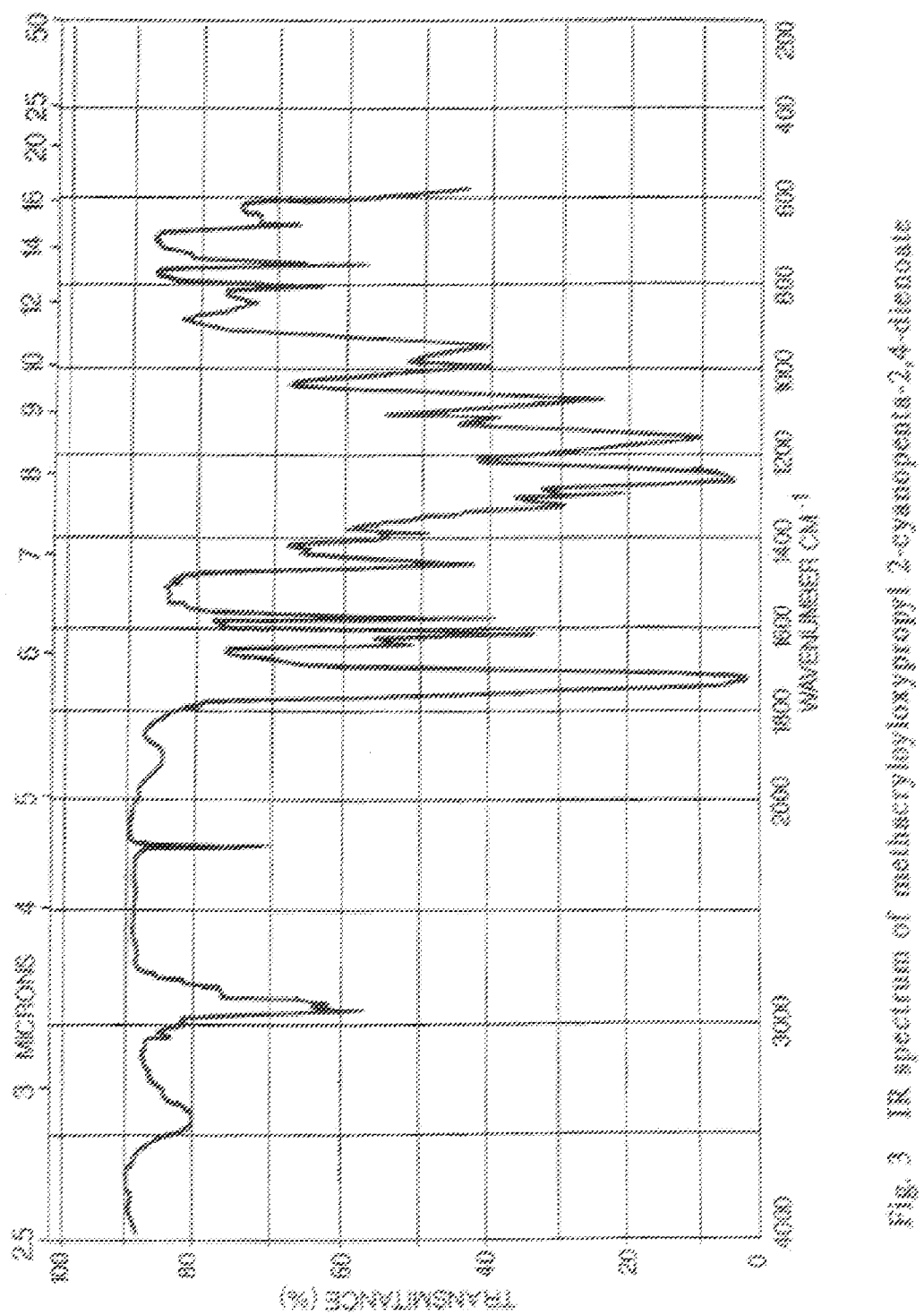
Fig. 3 IR spectrum of methacryloyloxyethyl 2-cyanopenta-2,4-dienoate

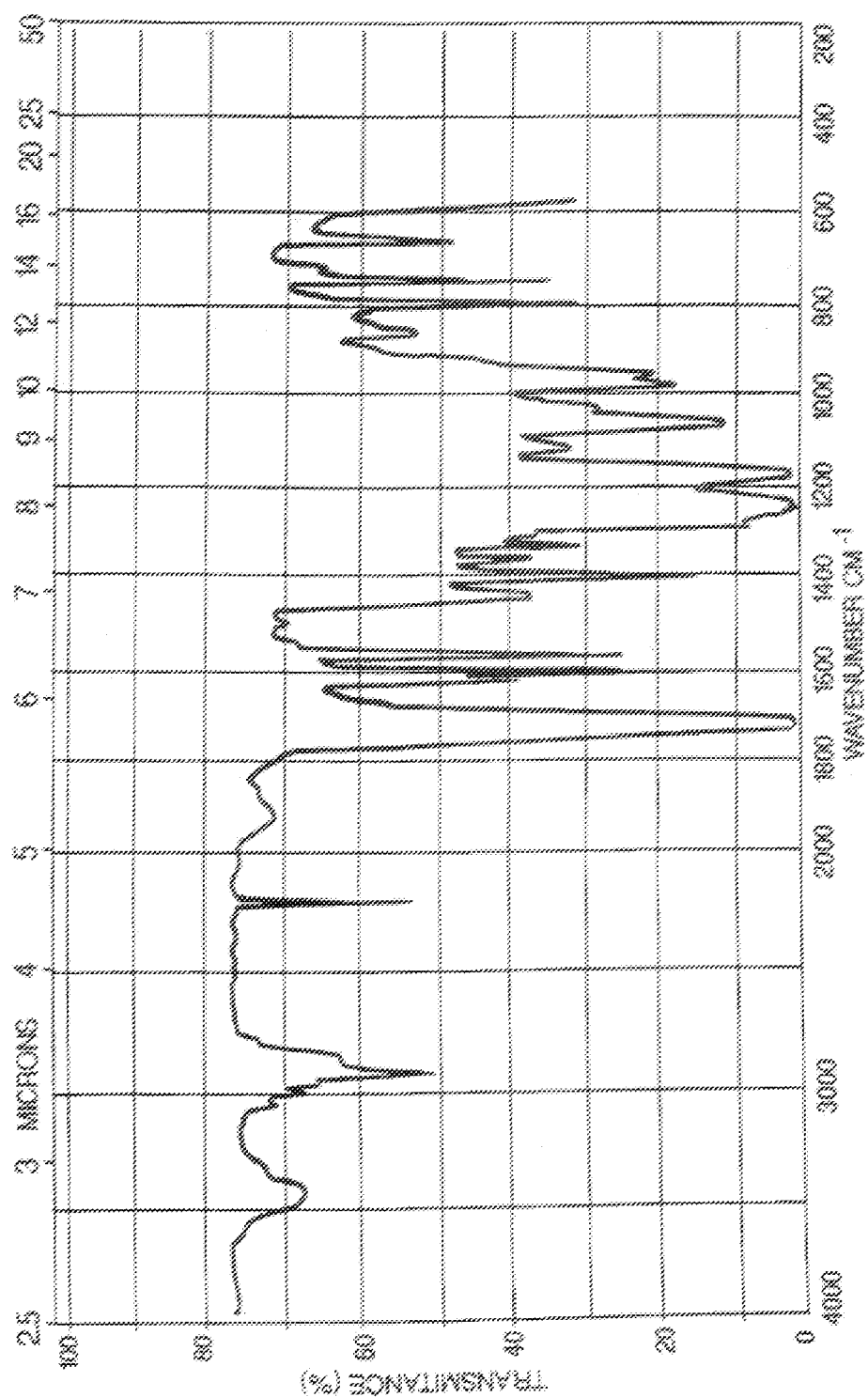
Fig. 4 IR spectrum of acryloyloxyethyl 2-cyanopenta-2,4-dienoate

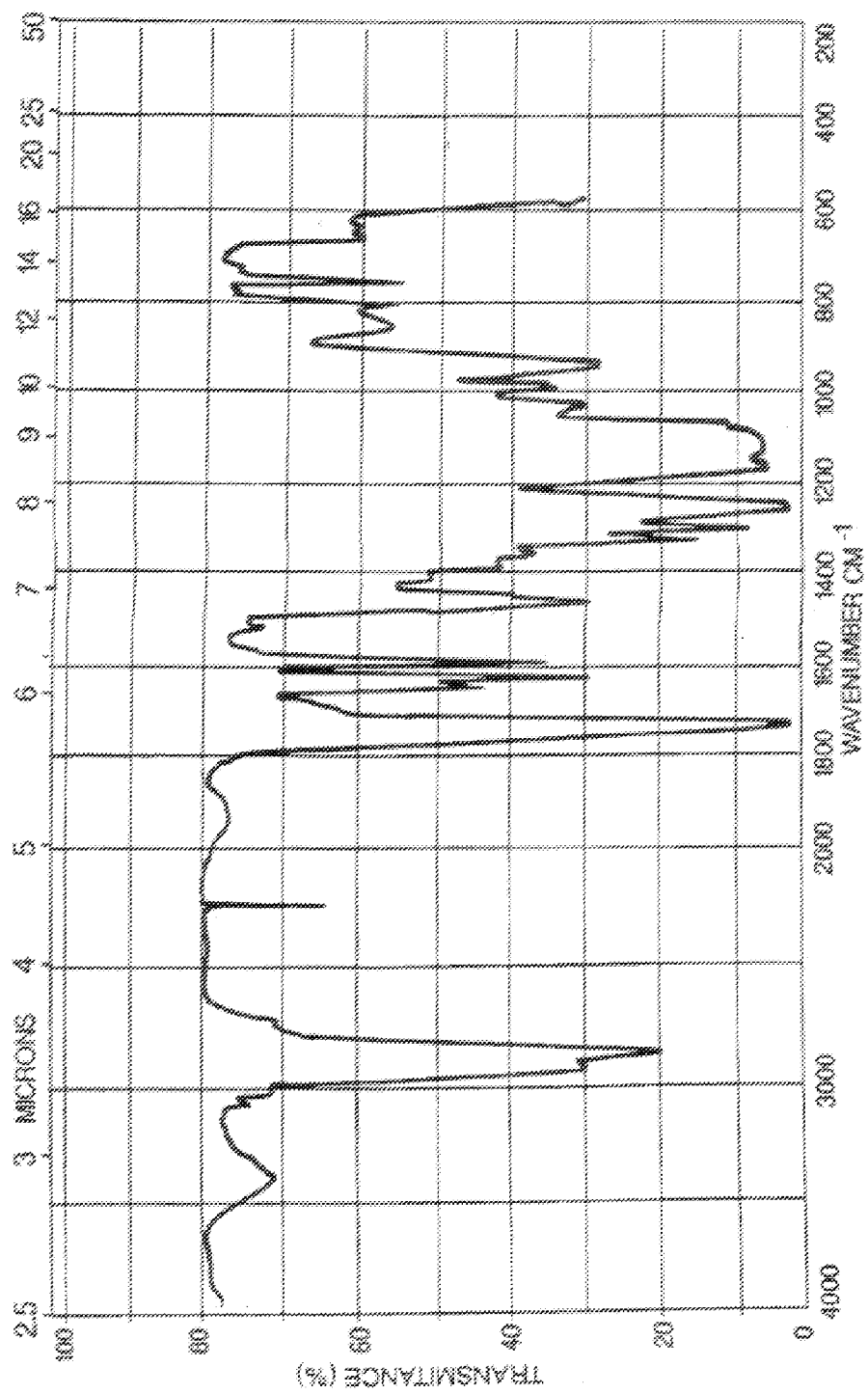
Fig. 5 IR spectrum of methacryloylhexa(oxyethyl) 2-cyanopenta-2,4-dienoate

ACRYLIC ESTERS OF 2-CYANO-2, 4 PENTENEDIOIC ACID

RELATED APPLICATIONS

This application is a Continuation of U.S. patent application Ser. No. 09/131,275, filed Aug. 10, 1998, now abandoned entitled "ACRYLIC ESTERS OF 2-CYANO-2,4 PENTENEDIOIC ACID," which claims priority to provisional application No. 60/055,791 filed Aug. 15, 1997. The contents of all of the foregoing applications are incorporated herein by reference in their entirety.

This invention relates to reactive monomers containing 2-cyanopenta-2,4-dienoate and methacrylic or acrylic double bonds in their molecules and the adhesives and polymers thereof.

Esters of the 2-cyanopenta-2,4-dienoic acid have been reported in the patent literature. The ethyl U.S. Pat. No. 3,316,227), alkenyl and alkoxyalkyl (U.S. Pat. No. 3,554,990) esters have been particularly described. These monomers can polymerize under the influence of weak alkali and are suitable for adhesives. Their use as modifiers to cyanoacrylate adhesives (U.S. Pat. No. 4,425,471) and for the manufacture of photoresists (EP 0404 446 A2) has also been reported.

The present invention provides reactive monomers containing 2-cyanopenta-2,4-dienoic and methacrylic or acrylic double bonds, the polymers and adhesives thereof. The monomers of the present invention have the formula:

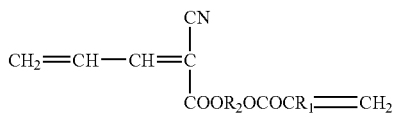

where $R_1$ is H or $CH_3$, $R_2$ is alkyl, alkenyl, alkynyl, alkoxyalkyl, poly(oxyalkyl), aryl, cyloalkyl or an aromatic heterocyclic radical. $R_2$ may also be one of the foregoing moieties substituted with one or more other of the moieties; this includes the case of a substituent itself being substituted. Group $R_2$ may contain other compatible constituents, for example alkoxy, alkoxyalkoxy, carbalkoxyalkyl or halogen. In general, $R_2$ can be any moiety which does not contain a sufficiently nucleophilic group to initiate polymerization or sufficiently electrophilic group to interfere with polymerization. The alkyl or alkenyl moiety may be cyclic and normally $R_2$ contains from 1 to 16 carbon atoms and often is a 1C, 2C, 3C, 4C, 5C, 6C, 7C or 8C group, more usually it is a 1C–6C group. In the case of moieties containing a heterocycle, heteroatom ring members are normally counted as a carbon atom.

More preferably, $R_2$ is alkyl, alkoxyalkyl, poly(oxyalkyl), halogenated alkyl, alkenyl, alkynyl, phenyl, halogenated phenyl, phenyalkyl, alkoxyalkyl, alkoxyalkoxyalkyl, carbalkoxyalkyl or alkylideneglyceryl, wherein the terms "alkyl" and "alkenyl" include the corresponding cyclic radicals.

Specific examples of $R_2$ are

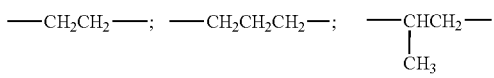

-continued

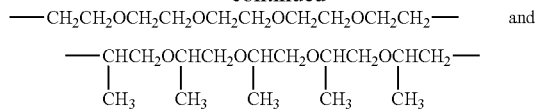

The reactive monomers of this invention are obtained by reacting acrolein with

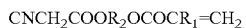

where $R_1$ and $R_2$ are the same radicals as described above. The methacrylated or acrylated cyanoacetates are in turn produced by reacting cyanoacetic acid with hydroxylterminated methacrylate or acrylate monomer or by transesterifying methyl or ethyl cyanoacetate with hydroxylterminated methacrylate or acrylate monomer. A preceding UK patent application by the same authors (UK Pat Application No GB 96 06327D) describes the synthesis and properties of these methacrylated and acrylated cyanoacetates and could be followed to obtain the raw materials. The reaction of acrolein with methacrylated or acrylated cyanoacetates is chemically consistent in nature to the reaction of acrolein with active methylene compound as described in U.S. Pat. No. 3,316,227. All of the considerations derived in this reference hold true for the present reaction between acrolein and methacrylated or acrylated cyanoacetates.

A distinctive feature of the present reaction however, is the reactivity of the active methylene compound which in the present case contains polymerizable methacrylic or acrylic bonds. Thus in order to avoid polymerization during the reaction it is advisble to use phenolic-type inhibitors, like hydroquinone and p-methoxyphenol, in conjunction with air sparge of the reaction mixture.

If desired mixtures of two or more of the monomers of the invention with themselves or other monomers or polymers could be used.

Usually the reactive monomers of the present invention are stabilized with anionic and free-radical polymerization inhibitors. Anionic polymerization inhibitors could be soluble acidic gases (for example sulfur dioxide), hydrogen fluoride, phosphonic, carboxylic and organic sulfonic acids, sultones, $BF_3$ and its complexes and phosphazenes, for example. The free-radical polymerization inhibitors are usually hydroquinone, p-methoxyphenol or t-butyl catechol, for example.

The inhibitors are normally used in small amounts of from 0.00001 to 1% by weight of the monomer. The preferred quantities for the above-mentioned inhibitors are: acidic gases—from 0.0001% to 0.06%; acids—from 0.0001% to 0.01%; sultones—from 0.01% to 0.1%; $BF_3$—from 0.0001 to 0.01; phosphazenes—from 0.00001% to 0.001%; free-radical inhibitors—from 0.001% to 1%. The foregoing percentages are percentages by weight of the reactive monomer. It should be noted that the quantity of inhibitor will influence the onset of polymerization of the monomers of the present invention and could be used as a means to control the set time.

The reactive monomers of the present invention may contain polymerization initiators. They could be anionic polymerization initiators like pyridine, aminopyridine, vinylpyridine, methoxyethylpyridine, piperidine, picoline, lutidine, N,N-dimethyl-p-toluidine, N—N-dimethyl-o-toluidine, N,N-dimethyl-m-toluidine, triphenylphosphine, triethylphosphine, tribenzylamine, triethylamine, benzyldimethylamine, diethylenetriamine, benzyltriethylamine, tribenzylamine, poly(4-vinylpyridine), calixarenes, tertiary amine-$SO_3$ complexes, polyethyleneglycol, phenolformaldehyde resins, vinylimidazole, triethanolaminatotitanium, aminosilanes, phosphites, metal acetylacetonates, N-(oxydiethylene) benzothiazole-2-sulfenamide, bismuth dimethyldithiocarbonate, as well as alcohols, bases and hydroxyl or amine group containing compounds.

They could also be cationic polymerization initiators. Free-radical polymerization initiators such as methylethylketone peroxide, cyclohexyl peroxide, cumene hydroperoxide, dibenzoyl peroxide or redoxy systems for generating free-radicals can be used. They are well known in the art of polymerizing acrylate and methacrylate monomers. Compounds which generate radicals or ions under ultraviolet or electron-beam irradiation could also be used to initiate polymerization of the reactive monomers of the present invention. The various initiators could be used alone or in conjunction with each other. In order to impart desired properties to the monomers of the present invention and to the properties of the resultant adhesive bond or polymer as well as for economic considerations, further additives can be introduced into them. They can be, for example, any of the known polymeric thickeners and viscosity regulators, rubbers, plasticizers and tougheners, compatibilizers, thixotropic agents, colourants, deodorants or perfumes, for example, used in cyanoacrylate adhesives and in acrylic and methacrylic ester compositions and polymers. The composition may also contain other monomers containing a reactive double bond.

A distinctive feature of the reactive monomers of the present invention is that they are easily polymerizable in a variety of ways. Anionic initiation, most commonly induced by the adsorbed on the objects' surface moisture causes polymerization along the dienic double bonds, yielding a polymer of substituted butadiene structure. The pendant acrylic or methacrylic double bonds can be additionally polymerized by heat, redoxy systems or UV or EB irradiation to yield a cross-linked elastomeric structure. In a different route of curing the acrylic or methacrylic double bonds could be polymerized initially yielding a polymethacrylate or polyacrylate with pending cyanopentadienic double bonds. They in turn could be polymerized by heat or moisture to produce similar to the first instance cross-linked structure. The following scheme illustrates the curing reaction that the monomers of the present invention could undergo.

A distinctive feature of the reactive monomers of the present invention is that as a result of polymerization they can form strong adhesive bonds between a variety of substrates, ie metals, plastics, rubbers, glass, wood, paper, live soft or bone tissue. They can cure in a matter of seconds to minutes. Depending on the type and degree of cure the adhesive bond can vary from soft and rubbery to tough and resilient. A distinctive characteristic of the adhesive bond is that as a consequence of cross-linking it is water and humidity resistant, heat resistant, impact and peel resistant and can sustain large loads and stresses.

Application of the reactive monomers of the present invention is in structural and industrial adhesives.

Another distinctive feature of the reactive monomers of the present invention is that they spread easily over water or biological fluids and then form a polymeric layer. This property can be employed to utilize these monomers as medical and surgical adhesives, particularly for bonding bone tissue in which case the initial anionic polymerization could be followed by radical cross-linking to obtain cross-linked adhesive bond capable of sustaining the loads at the fractured interface.

Another application of the reactive monomers of the present invention is for coatings which can be produced by surface moisture cure or by UV-light irradiation. They will be particularly suitable for optical fibre coating.

Another application of the reactive monomers and polymers thereof of the present invention is for manufacture of positive or negative photo or electron beam resists. Their controlled step-wise polymerization will produce ultra-high resolution.

The above-mentioned applications are only indicative and do not limit the scope of application of the reactive monomers of the present invention, as well as the applications of their adhesives and polymers.

The invention is illustrated by the following examples:

EXAMPLE 1

21.9 g of methacryloyloxyethyl cyanoacetate is mixed together with 40 ml of tetrahydrofuran. The mixture is cooled to 4° C. and 9 g of zinc chloride is added during mixing. The mixture is cooled again to 4° and 8.9 ml of acrolein are added dropwise over 5 minutes. The temperature increases from 4° C. to 8° C. The reaction flask is removed from the ice water bath and left stirring for 8 hours at room temperature. To the clear yellow solution obtained 50 ml of toluene is added. The product is isolated by three consecutive extractions with 100 ml of 2N hydrochloric acid. The organic layer is filtered through filter paper. The filtrate is stripped from the solvent by heating (90° C.) under reduced pressure (0.7 mmHg). A steady stream of air through a capillary is maintained during the stripping stage. 23.0 g of methacryloyloxyethyl 2-cyanopenta-2,4-dienoate are obtained. Its $n_D^{20}$=1,5139. IR spectrum (FIG. 2) confirms the structure. A drop of the product placed on water spreads and forms a polymeric film. A drop of product placed between fingers, glass or metal surfaces polymerizes instantly to give an adhesive bond.

EXAMPLE 2

35.2 g of methacryloyloxypropyl cyanoacetate is mixed with 50 ml of dioxane. 13.5 g of zinc chloride is added during mixing. 13,25 g of acrolein are added dropwise over 10 minutes, taking care the reaction temperature not to exceed 20° C. The stirring is continued for a further 8 hours at room temperature yielding a clear yellow solution. 100 ml of methylmethacrylate are mixed in and then three consecutive extractions with 150 ml of 2N hydrochloric aced are performed. The organic layer is filtered and stripped under reduced pressure (0.7 mm Hg). The pot temperature is not to exceed 90° C. and a steady stream of air through the product is maintained during stripping. 25 g of methacryloyloxypropyl 2-cyanopenta-2,4-dienoate are obtained with $n_D^{20}$=1,5045. The IR spectrum (FIG. 3) confirms the chemical structure. The product possesses the same adhesive properties as described in Example 1.

EXAMPLE 3

20.4 g of acryloyloxyethyl cyanoacetate containing 0.02 g of p-methoxyphenol are mixed together with 40 ml of tetrahydrofuran. Through a capillary a constant flow (4 ml/min) of dry air is sparged through the reaction mixture during the reaction. The mixture is cooled to 4° C. and 9.5 g of zinc chloride are added during mixing. The mixture is cooled again to 4° C. and 8.9 ml of acrolein are added dropwise over 5 minutes. The reaction temperature increases to 9° C. The reaction flask is removed from the ice water bath and left stirring for 8 hours at room temperature. To the clear yellow solution obtained 50 ml of toluene are added and the product is isolated by three consecutive extractions with 100 ml of 2N hydrochloric acid solution. The organic layer is filtered and stripped from solvents by heating up to 90° C. under reduced pressure of 0.7 mm Hg. A stream of air through a capillary is maintained during the stripping stage. 13.3 g of acryloyloxyethyl 2-cyanopenta-2,4-dieonate with $n_D^{20}=1,5147$ are obtained. The IR spectrum (FIG. 4) confirms the chemical structure.

EXAMPLE 4

23.17 g of methacryloylhexa(oxyethyl)cyanoacetate containing 0.035 g of hydroquinone are mixed together with 33 ml of dioxane. Through a capillary a constant flow (4 ml/min) of dry air is started and maintained during the reaction process. 4.5 g of zinc chloride are added during stirring. The mixture is cooled to 20° C. and 4.45 ml of acrolein are added dropwise over 5 minutes. The mixing is continued at room temperature for 12 hours. To the clear yellow solution 100 ml of methyl methacrylate are added. The product is isolated by three consecutive extractions with 100 ml of 2N hydrochloric acid solution. The organic layer is filtered and subjected to stripping by heating up to 90° C. under vacuum of 0.7 mm Hg and the essential stream of dry air. 18 g of methacryloyl(oxyethyl) 2-cyanopenta-2,4-dienoate, with $n^{20}=1,4964$ are obtained. The IR spectrum (FIG. 5) confirms the chemical structure.

EXAMPLE 5

Adhesive bonds based on the reactive monomers of the present invention were prepared by placing a drop of monomer on one metal surface to which the other was manually pressed for 1 minute. Adhesive strength was measured after 24 hours and after ageing for 24 hours at various temperatures. The specimen had dimensions in accordance with ASTM D1002 for the sheer strength and ASTM D897 for the tensile strength determinations. The steel surfaces were roughened with extra fine sandpaper and degreased with methylene chloride. No chemical treatment of the surfaces was employed. The testing procedure followed the above mentioned standards. Each reported value is average of 10 determinations. The obtained results are summarized in Table 1.

TABLE 1

Adhesive strength of steel/steel joints bonded with methacrylated and acrylated 2-cyanopenta-2,4-dienoates

| No | 2-cyanopenta-2,4-dienoate | Mode of testing | Adhesive strength (kg/cm2) after 24 h at | | | | |
|---|---|---|---|---|---|---|---|
| | | | 20° C. | 100° C. | 125° C. | 150° C. | 200° C. |
| 1 | methacryloyloxyethyl | tensile | 70 | 172 | 184 | 77 | 62 |
| | | shear | 56 | 123 | 132 | 61 | 61 |
| 2 | methacryloyloxypropyl | tensile | 54 | 77 | 100 | 46 | 18 |
| | | shear | 39 | 112 | 69 | 66 | 48 |
| 3 | acryloyloxyethyl | tensile | 52 | 121 | 232 | 161 | 178 |
| | | shear | 35 | 120 | 112 | 108 | 76 |
| 4 | acryloyloxypropyl | tensile | 36 | 78 | 130 | 158 | 148 |
| | | shear | 20 | 135 | 117 | 149 | 107 |
| 5 | methacryloylhexa(oxyethyl) | tensile | 19 | 27 | 28 | 28 | 43 |
| | | shear | 10 | 12 | 37 | 38 | 38 |
| 6 | methacryloylpenta(oxypropyl) | tensile | 6 | 10 | 14 | 16 | 60 |
| | | shear | 7 | 10 | 14 | 19 | 65 |

EXAMPLE 6

Adhesive bonds between glass/glass and glass/steel were prepared in the same fashion as described in Example 5. The glass surface was only degreased with methylene chloride. The glass/glass joints and the glass portion of the glass/steel joints were in turn bonded in larger areas to steel coupons so that they rather than the fragile glass could be gripped in the testing machine. The obtained results are presented in Table 2.

TABLE 2

Glass joints bonded with methacrylated and acrylated cyanopentadienoates

| No | 2-cyanopenta-2,4-dienoates | Substrates | Mode of testing | Adhesive strength (kg/cm2) after 24 h at | | | | |
|---|---|---|---|---|---|---|---|---|
| | | | | 20° C. | 100° C. | 150° C. | 200° C. | 250° C. |
| 1 | methacryloyloxyethyl | glass/glass | tensile | 69 | NT | NT | NT | NT |
| | | glass/steel | tensile | 150 | NT | NT | NT | NT |

TABLE 2-continued

Glass joints bonded with methacrylated and acrylated cyanopentadienoates

| No | 2-cyanopenta-2,4-dienoates | Substrates | Mode of testing | Adhesive strength (kg/cm2) after 24 h at | | | | |
|---|---|---|---|---|---|---|---|---|
| | | | | 20° C. | 100° C. | 150° C. | 200° C. | 250° C. |
| 2 | methacryloyloxypropyl | glass/glass | tensile | 35 | NT | NT | NT | NT |
| | | glass/steel | tensile | 134 | NT | NT | NT | NT |
| 3 | acryloyloxyethyl | glass/glass | shear | >20* | >20* | >20* | >15* | NT |
| | | glass/steel | tensile | 47 | 35 | 13 | 6 | NT |
| 4 | methacryloylhexa(oxyethyl) | glass/glass | tensile | 5 | 22 | 21 | 20 | NT |
| | | glass/glass | shear | >20* | >20* | >20* | >20* | NT |
| | | glass/steel | tensile | 11 | 12 | 13 | NT | NT |
| 5 | methacryloylpenta(oxypropyl) | glass/glass | tensile | 4 | 4 | 4 | 13 | 22 |
| | | glass/steel | shear | 3 | 3 | 8 | >20* | >20* |
| | | glass/steel | tensile | 5 | 5 | 27 | 38 | 35 |

NT—not tested
*glass substrate failure

EXAMPLE 7

Various substrates were bonded with acryloyloxyethyl 2-cyanopenta-2,4-dienoate following the described procedure. The obtained results are presented in Table 3.

TABLE 3

Adhesive strength of various substrates bonded with acryloyloxyethyl 2-cyanopenta-2,4-dienoate

| No | Substrates | Mode of testing | Adhesive Strength (kg/cm2) after 24 h at | | | | |
|---|---|---|---|---|---|---|---|
| | | | 20° C. | 55° C. | 80° C. | 100° C. | 150° C. |
| 1 | balsa wood/balsa wood | shear | 12 (c) | >20 (s) | | | |
| 2 | paper/paper | shear | >3.5 (s) | | | | |
| 3 | carton/carton | shear | >5 (s) | | | | |
| 4 | teflon/teflon | shear | 3 (c) | | | 7 (a) | 7 (a) |
| 5 | polypropylene/polypropylene | shear | 3 (c) | 12 (a) | 15 (a) | | |
| 6 | polycarbonate/polycarbonate | shear | 14 (c) | | | 20 (a) | 41 (c) |
| 7 | UPVC/UPVC | shear | 11 (c) | | 14 (a) | | |
| 8 | polyacrylate/polyacrylate | shear | 6 (c) | 25 (a) | | | |
| 9 | steel/polyacrylate | shear | 24 (c) | | | 35 (a) | |
| | | tensile | 48 (c) | | | 56 (a) | |
| 10 | steel/UPVC | shear | 8 (a) | | | 37 (a) | |
| | | tensile | 16 (a) | | | 34 (a) | |
| 11 | steel/polycarbonate | shear | 21 (a) | | | 32 (c) | |
| | | tensile | 30 (a) | | | 15 (a) | 15 (a) |
| 12 | steel/teflon | shear | 5 (a) | | | 6 (a) | 6 (a) |
| 13 | steel/polypropylene | shear | 15 (a) | 21 (a) | | 31 (a) | |
| 14 | steel/polyethylene | shear | 4 (c) | 37 (a) | | | |
| | | tensile | 5 (c) | 27 (a) | | | |

(s)—substrate fails
(c)—cohesive type of bond failure
(a)—adhesive type of bond failure

EXAMPLE 8

UV light curable compositions were prepared by dissolving into the reactive monomers of the present invention 1% by weight of 1-hydroxy-cyclohexyl-phenyl-ketone. A drop of the composition was spread between glass/glass or glass/steel surfaces and subjected to UV radiation (with intensity of 7 mW/cm$^2$ at 365 nm and 4 mW/cm$^2$ at 310 nm) for 2 minutes. The stregnth of the obtained adhesive bonds were measured following the irradiation and also following additional thermal treatment for 24 hours. The obtained results are presented in Table 4.

TABLE 4

Glass joints bonded by UV-cured cyanopentadienoate monomers

| No | 2-cyanopenta-2,4-dienoate | Substrates | Testing mode | Adhesive bond strength (kg/cm$^2$) | | | |
|---|---|---|---|---|---|---|---|
| | | | | 20° C. | 100° C. | 150° C. | 200° C. |
| 1 | acryloyl-oxyethyl | glass/glass | shear | >20 (s) | >20 (s) | >20 (s) | >20 (s) |
| | | | tensile | 11 (a) | 42 (s) | >41 (s) | >40 (s) |
| | | glass/steel | shear | 14 (a) | >18 (s) | >17 (s) | >17 (s) |
| | | | tensile | 25 (a) | 63 (a) | 38 (a) | 36 (a) |
| 2 | methacryloyl-penta(oxypropyl) | glass/steel | tensile | 7 (c) | 13 (a) | 39 (a) | 38 (a) |

(s)—substrate fails
(a)—adhesive type of bond failure
(c)—cohesive type of bond failure

The invention claimed is:

1. Adhesive and coating compositions containing reactive monomers of the formula:

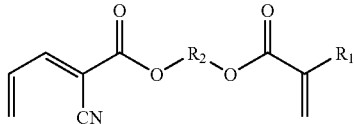

wherein R$_1$ is H or CH$_3$ and R$_2$ is a substituted or unsubstituted alkyl, alkenyl, alkynyl, alkoxyalkyl, poly(oxyalkyl), aryl, cycloalkyl, heterocyclyl radical wherein the substituent when present is at least one alkyl, alkenyl, alkynyl, alkoxyalkyl, poly(oxyalkyl), aryl, cycloalkyl, heterocyclyl radical or halogen and wherein the monomer is a liquid at ambient temperature.

2. A reactive monomer composition comprising:
the reactive monomer of the formula:

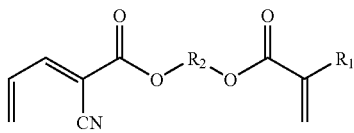

wherein R$_1$ is H or CH$_3$ and R$_2$ is a substituted or unsubstituted alkyl, alkenyl, alkynyl, alkoxyalkyl, poly(oxyalkyl), aryl, cycloalkyl, heterocyclyl radical wherein the substituent when present is at least one alkyl, alkenyl, alkynyl, alkoxyalkyl, poly(oxyalkyl), aryl, cycloalkyl, heterocyclyl radical or halogen and wherein the monomer is a liquid at ambient temperature; and
a stabilizer against polymerization,
wherein the stabilizer is a free radical polymerization inhibitor,
present in an amount of from 0.001% to 1% by weight of the monomer or an anionic polymerization inhibitor present in an amount of from 0.00001% to 1% by weight of the monomer.

3. Compositions based on reactive monomers of claim 1 containing polymeric thickeners, viscosity regulators, plasticizers thixotropic agents, compatibilizers, adhesion promoters, pigments, colourants, fillers, deodorants and perfumes.

4. Compositions based on reactive monomers of claim 1 containing other monomers with a reactive bond, including but not limited to cyanoacrylates.

5. The reactive monomer composition according to claim 2, wherein the free-radical polymerization inhibitor is hydroquinone, p-methoxyphenol, or t-butyl cathecol.

6. The reactive monomer composition according to claim 2, wherein the anionic polymerization inhibitor is sulphur dioxide, hydrogen fluoride, phosphoric acid, phosphonic acid, sulfuric acid, sulphonic acid, carboxylic acid, organic sulfonic acid, sultone, boron trifluoride, boron trifluoride complexes, or phosphazene.

* * * * *